United States Patent

Hannart

[11] 4,389,405
[45] Jun. 21, 1983

[54] 1,10-DIMETHYL-2,7-DIHYDROOXAYOHIMBANES AN ANTI-ARRHYTHMIC USE THEREOF

[75] Inventor: Jean A. Hannart, Dion Valmont, Belgium

[73] Assignee: Omnichem, S.A., Brussels, Belgium

[21] Appl. No.: 223,159

[22] Filed: Jan. 7, 1981

[30] Foreign Application Priority Data

Jan. 9, 1980 [BE] Belgium ............................... 198889

[51] Int. Cl.³ .................. A61K 31/475; C07D 495/00
[52] U.S. Cl. ...................................... 424/262; 546/50; 544/125; 544/364; 424/248.4; 424/250
[58] Field of Search ........................... 546/50; 424/262

[56] References Cited

FOREIGN PATENT DOCUMENTS 2135143 12/1972 France .

Primary Examiner—Donald G. Daus
Assistant Examiner—D. Springer
Attorney, Agent, or Firm—David S. Fishman

[57] ABSTRACT

Compounds having the following general formula:

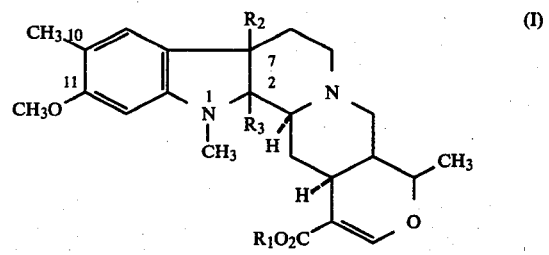

wherein R is an alkyl or aminoalkyl group having 1 to 8 carbon atoms, or a hydrogen atom; $R_2$ and $R_3$ are either hydrogen atoms or, together, an additional carbon-carbon bond, as well as the mineral or organic acid addition salts thereof. These compounds are used as anti-arhythmic agents.

8 Claims, No Drawings

1,10-DIMETHYL-2,7-DIHYDROOXAYOHIMBANES AN ANTI-ARRHYTHMIC USE THEREOF

BACKGROUND OF THE INVENTION

This invention relates to new five-ring derivatives of the oxayohimbane type methylated in position 10, the process for producing the same and the pharmaceutical compositions containing them.

SUMMARY OF THE INVENTION

The compounds of this invention have the following general formula:

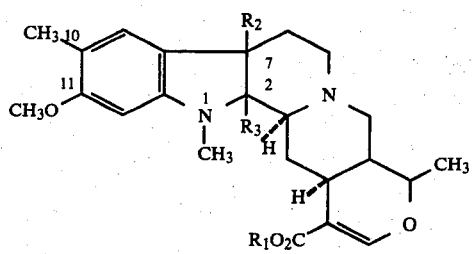

wherein R is an alkyl or aminoalkyl group having 1 to 8 carbon atoms, or a hydrogen atom; $R_2$ and $R_3$ are either hydrogen atoms or, together, an additional carbon-carbon bond, as well as the mineral or pharmaceutically acceptable organic acid addition salts thereof.

More particularly, the derivatives of this invention are 2,7-dihydrooxayohimbanes disubstituted on positions 10 and 11 of the aromatic ring.

DETAILED DESCRIPTION OF THE INVENTION

The starting compounds used in the process of the present invention are 11-methoxylated five-ring indolederivatives corresponding to formula II

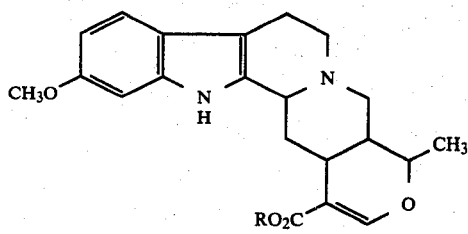

The compounds of the invention are more particularly obtained advantageously from tetraphylline of formula II wherein $R=CH_3$.

In fact, it has been shown that tetraphylline may be readily converted into esters of formula II wherein R is a group such as dimethyl-aminoethyl, morpholinoethyl, N-methylpiperazinoethyl or piperidinoethyl group (Belgian Pat. Nos. 69,950 and 780,854).

The tetraphylline itself is an alkaloid readily isolated in a large proportion from Rauwolfia roots (Djerassi, Fishman, Chem. Ind. 627, 1955).

Starting from the compounds of the invention having the formula I wherein $R_1$ is a methyl group, it has also been possible to obtain conventionally the corresponding tetraphyllinic acids which may be esterified to give compounds wherein $R_1$ is an alkyl or aminoalkyl group having 1 to 8 carbon atoms (see above mentioned Belgian Patents).

During the first step of the process of the invention, the tetraphylline is dissolved in a $C_1$-$C_3$ organic acid such as trifluoracetic acid and a hydride donor such as sodium borohydride or sodium cyanoborohydride is added to the reaction medium. By way of example, the added amount of sodium borohydride may vary between one half and two times the weight of the used tetraphylline.

The so obtained solution is cooled and an excess of formaldehyde is added. The formaldehyde will be advantageously in a 30–40% aqueous solution. During said addition, the temperature of the reaction mixture is preferably kept between 0° and 10° C.

At the end of the addition, a substantially identical amount of the hydride donor is still added and the mixture is then stirred for 5 minutes to 1 hour.

After addition of water, alkalinization, conventional extraction with a water immiscible solvent, concentration and recrystallization, the desired dimethyl-1,10-dihydro-2,7-methoxy-11-oxayohimbane is obtained with a yield varying between 55 and 90%.

The reaction sequence characterizing the above described process is conducted preferably in a single flask, the intermediates being not isolated.

The probable reaction mechanism is described by the following scheme:

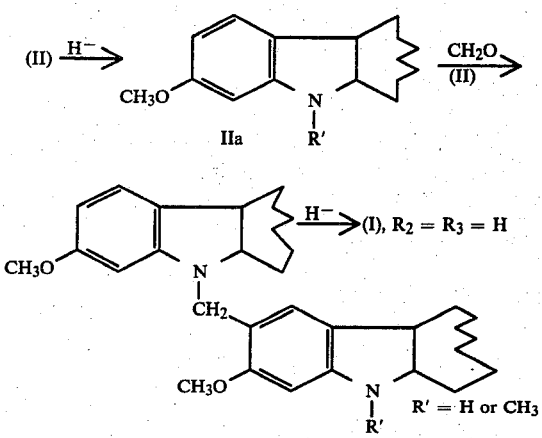

In addition, it is known that the dihydroindole derivatives of the oxayohimbane type may be readily dehydrogenated to give the corresponding indole derivatives (see, e.g. Belgian Pat. No. 796,521).

The said dehydrogenation may be advantageously applied to the derivatives of the invention, thereby giving new pharmacologically active compounds having the general formula I wherein $R_2$ and $R_3$=additional bond.

If desired, the N-substituted derivatives (II) dihydrogenated in positions 2 and 7 are thus dehydrogenated through methods such as the action of a dehydrogenation catalyst, e.g. a metal Pd, Pt, optionally on a carrier, in the presence of an hydrogen acceptor which may be oxygen or an unsaturated organic reagent such as maleic anhydride, or the action of metal combinations such as manganese dioxide, cupric chloride or potassium ferricyanide, or the action of dehydrogenation organic reagents such as quinones in an aromatic organic solvent such as benzene or toluene, or an etheroxide or aliphatic chlorinated hydrocarbon, at a low temperature.

The solvent may be a mixture of dioxane and ether and the dehydrogenation reagent may be dicyandichloroquinone (DDQ).

We have also observed an easy oxidation in the presence of atmospheric oxygen.

Pharmacological Properties and Use of the Compounds of the Invention

Numerous derivatives having the oxayohimbane skeleton from which the tetraphylline and the ajmalicine are derivated, have been found as compounds having interesting hypotensive, vasodilating and blood flow rate regulating properties. Thus, the French Pat. Nr. 72 10822 of the Applicant discloses the synthesis and the pharmacological properties of the aminoethyl derivatives of tetraphylline.

The compounds of the invention have been also found as being active in numerous pharmacological tests and, accordingly, they are likely to be used as active principle of medicaments. The derivatives of the invention may be also used as intermediate products for the synthesis of other therapeutically used substances.

Particularly, the dihydro-2,7-tetraphyllinate compounds of the invention have been found as being active as anti-arhythmic agents in the aconitine test.

This test has been carried out on anesthetized rats kept under artificial respiration and for which the electrocardiogram in three derivations DI, DII, DIII is continuously recorded.

For the control rats, the perfusion of aconitine solution causes ventricular extrasystoles (V.E.S.) after two or three minutes. The animals previously treated with anti-arhythmic drugs extend the latency of occurrence of these heart disorders.

The compounds I under base form are injected i.v. in a ±0.02 N HCl solution five minutes before the aconitine perfusion.

The following table gives the results obtained with four reference products (lidocaine, quinidine, ajmaline and aprindine) as compared with the results obtained with four compounds according to the present invention:

(Ia): 2-dimethylamino-ethyl dimethyl 1,10-dimethyl-2,7-dihydro-tetraphyllinate
(Ib): 2-(N-methylpiperazine-ethyl)1,10-dimethyl-2,7-dihydro-tetraphyllinate
(Ic): 2-piperidino-ethyl 1,10-dimethyl-2,7-dihydro-tetraphyllinate
(Id): 2-dimethylamino-ethyl 1,10-dimethyl-2,7-dihydro-tetraphyllinate

TABLE

| Reference products | Dosis I.V. moles/kg | Time elapsed until the occurrence of the first V.E.S. (in decimal minutes) $\overline{X}$ | s.d.a.* | Response in % of the time observed in the controls |
|---|---|---|---|---|
| LIDOCAINE | 36.93 | 3.12 | 0.17 | 119 |
| | 55.39 | 3.90 | 0.30 | 147 |
| | 73.86 | 4.21 | 0.27 | 186 |
| QUINIDINE | 13.39 | 3.38 | 0.29 | 127 |
| | 26.78 | 4.37 | 0.32 | 176 |
| | 40.17 | 4.48 | 0.33 | 198 |
| AJMALINE | 3.063 | 3.31 | 0.16 | 146 |
| | 6.126 | 3.94 | 0.27 | 168 |
| | 12.2512 | 5.32 | 0.31 | 235 |
| APRINDINE | 3.48 | 3.19 | 0.25 | 126 |
| | 6.97 | 5.70 | 0.45 | 225 |

TABLE-continued

| Reference products | Dosis I.V. moles/kg | Time elapsed until the occurrence of the first V.E.S. (in decimal minutes) $\overline{X}$ | s.d.a.* | Response in % of the time observed in the controls |
|---|---|---|---|---|
| | 13.93 | 8.88 | 1.22 | 351 |
| Ia | 2.66 | 3.80 | 0.33 | 152 |
| | 4.26 | 4.90 | 0.81 | 183 |
| | 5.32 | 5.16 | 0.68 | 204 |
| Ib | 1.525 | 4.25 | 0.23 | 158 |
| | 3.049 | 5.24 | 0.58 | 207 |
| Ic | 1.32 | 3.49 | 0.35 | 138 |
| | 1.98 | 4.10 | 0.31 | 169 |
| | 2.65 | 4.43 | 0.33 | 186 |
| Id | 0.88 | 4.23 | 0.67 | 154 |
| | 1.77 | 5.33 | 0.56 | 194 |
| | 2.66 | 9.19 | 1.85 | 334 |

*s.d.a. Sum of deviations from average

The compounds of the invention and, more particularly the compound Id have been found as having an equal or higher activity than the reference compounds well known for their good anti-arhythmic activity.

The LD$_{50}$ i.g. for the compound Id is 406 mg/kg (mice), said dosis being determined graphically according to the Lichtfield and Wilcoxon Method (J. Pharmacol. Exp. Ther., 1946, 96, 99).

The following examples are illustrating the features of the invention without any limitation:

EXAMPLE 1

1,10-dimethyl-2,7-dihydro-tetraphylline 1.4 g of NaBH$_3$CN or NaBH$_4$ are added in small portions to a solution of 2 g of tetraphylline in 50 ml of trifluoracetic acid.

After cooling in an ice bath, 20 ml of 37% aqueous formaldehyde are added. The rate at which the aldehyde is introduced, is adjusted so that the temperature of the medium is kept lower than +10° C. The reaction is continued through the addition of 1 g of NaBH$_3$CN or NaBH$_4$. After stirring for 10 minutes, the mixture is flooded with ice water, alkalized with diluted ammonia and extracted three times with 200 ml of CH$_2$Cl$_2$. The dried, filtrated and dry evaporated organic phase gives a residue (2.63 g) crystallizing in methanol.

Thus, 1.89 g (87%) of the pure derivated compound are obtained.

Melting point: 200.5° C.
α$_D$: +86.6 (CHCl$_3$; c=0.25)
U.V. (methanol) max: 213 (4.48); 241 (4.24); 303 (3.73). min: 229 and 276.
I.R. (KBr): 1620, 1705 cm$^{-1}$.
Mass spectrum: 412 (M+); 397;381;262;242;238;237;236;226;225;224;222;210;209;2-02;188;168;154;150;149;139;132;122.

NMR of $^1$H: signals at ppm: 7.56 s(1H) C$_{(17)}$H; 6.83 s(1H) C$_{(12)}$H; 6.24 s(1H) C$_{(9)}$H; 3.78 s(3H) C$_{(11)}$OCH$_3$; 3.70 s(3H) COOCH$_3$; 2.86 s(3H) N$_{(1)}$-CH$_3$; 2.16 s(3H) C$_{(10)}$-CH$_3$; 1.12 d(3H) C$_{18}$-H (J=7 Hz).

EXAMPLE 2

1,10-dimethyl-2,7-dihydro-tetraphyllinic acid 15 g of 1,10-dimethyl-2,7-dihydro-tetraphylline suspended in a mixture of 150 ml of methanol and 150 ml of 5% NaOH are refluxed under an argon atmosphere. After 2 h 30, the total solubilization is obtained and the saponification is completed. The medium is cooled and the alcohol is expelled through vacuum distillation.

The pH is then lowered down to about 6.5 through the addition of 50% aqueous acetic acid. An abundant white precipitate is filtered off, rinsed with distilled water and dried under vacuum at 80° C. for 2 hours. The resulting 13.9 g (namely a yield of 96%) of raw acid are recrystallized in a mixture of methanol and methylene chloride.

Melting point: 284°–288° C. ($CH_2Cl_2$-$CH_3OH$)

U.V. (methanol; c=10.196 mg/l) max: 209 (4.60); 301 (3.69). inflexion: 240 (4.17). min: 275 (3.19).

I.R. (KBr): 3420, 2460, 1670 and 1600 $cm^{-1}$.

EXAMPLE 3

2-dimethylamino-ethyl 1,10-dimethyl-2,7-dihydro-tetraphyllinate (Ia)

For a period of 45 minutes, 9.7 g of $NaBH_3CN$ are added in small portions to a solution of 13.78 g of dimethylaminoethyl tetraphyllinate in 345 ml of trifluoracetic acid. After cooling with an ice bath, 138 ml of 37% formaldehyde, then 6.9 g of $NaBH_3CN$ are added dropwise. A vigorous agitation and an argon stream are necessary to prevent the ignition of $NaBH_3CN$.

The mixture is poured on ice, alkalized with ammonia, then depleted with methylene chloride. The extracts are washed with water, dried and dry vacuum evaporated, thereby giving a residue (11.67 g or 79%) which is recrystallized in methanol or ether.

Melting point: 187°–188° C. (methanol)

$a_D$: +80° (c=0.25; $CHCl_3$)

U.V. (methanol) c: 14.95 mg/l: max: 212(4.50);242(4.32); 301(3.85). min: 228(4.25);275(3.38).

I.R. (KBr) bands at 1695 and 1610 $cm^{-1}$

N.M.R.: 7.62, s.,1H, $C_{(17)}H$; 6.87,s.,1H,$C_{(12)}H$; 6,27,s.,1H,$C_{(9)}H$; 4.27,t.,J=6 cps,2H,$CO_2CH_2$; 3.83,s.,3H,$C_{(11)}$-$OCH_3$; 2.90,s.,3H,N-$CH_3$; 2.32,s.,6H.-$N(CH_3)_2$; 2.13,s.,3H,$C_{(10)}CH_3$; 1.13,d.,J=7 cps,3H,$C_{(18)}H_3$.

M.S.: $M^+$ at 469.

EXAMPLE 4

2-dimethylamino-ethyl 1,10-dimethyl-2,7-dihydro-tetraphyllinate (Id)

For a period of 1 hour, 13.1 g of $NaBH_3CN$ are added to a solution of 18.40 g of diethylaminoethyl tetraphyllinate in 460 ml of trifluoracetic acid. Fifteen minutes after the end of the reactive addition, the mixture is cooled at 0° and 184 ml of 37% aqueous formaldehyde solution are added. After stirring for 15 minutes at room temperature, 9.2 g of $NaBH_3CN$ are added in small portions. The mixture is poured on ice, alkalized with ammonia and depleted with $CH_2Cl_2$.

After washing with water, drying and dry evaporation, the organic phases leave a residue weighing 17.23 g which, after crystallization in acetone, gives 9.1 g of crystals.

Melting point: 121°–122° C. (acetone)

$a_D$: +88° (c=0.25; $CHCl_3$)

U.V. (methanol) c: 15.2 mg/l: max: 243 (4.26);302(3.71) min: 228 (4.15);275(2.23).

I.R. (KBr) bands at 1690, 1610, 818, 765 (aromatic 1,2,4,5-tetrasubstituted)

N.M.R. ($CDCl_3$): 7.60 (s,1H,$H_{17}$); 6,88 (s,1H,$H_{12}$); 6.45 (s,1H,$H_9$); 4.25 (t,2H,$CO_2CH_2$); 3.85 (s,3H,$OCH_3$); 2.93 (s,3H,N-$CH_3$); 2.17 (s,3H,Ar-$CH_3$); 1.17 (d,7$H_2$,3H,$C_{18}H_3$); 1.07 (t,6H,$CH_2$-$CH_3$)

M.S.: $M^+$ at 497.7; 381, 309; 294; 188; 160; 100; 86.

EXAMPLE 5

2-morpholinoethyl 1,10-dimethyl-2,7-dihydro-tetraphyllinate

For a period of 30 minutes, 7.7 g of $NaBH_3CN$ are added in small portions to a solution of 11 g of ethylmorpholine tetraphyllinate in 275 ml of trifluoracetic acid. After cooling with an ice bath, 110 ml of 37% formaldehyde, then 5.5 g of $NaBH_3CN$ are added dropwise. A very vigorous agitation and an argon stream are necessary to prevent the ignition of $NaBH_3CN$. The mixture is poured on ice, alkalized with ammonia, then depleted with methylene chloride. After washing with water, drying on $MgSO_4$ and dry vacuum evaporation, the extracts give a residue (8.96 g or a yield of 80%) which is recrystallized in methanol.

Melting point: 169°–170° C. (methanol)

$a_D$: +75° (c=0.25; $CHCl_3$)

U.V. (methanol) c=19.96 mg/l: max: 211(4.54); 242(4.29); 301(3.78). min: 228(4.21); 274(3.15).

I.R. (KBr): bands at 1615 and 1705 $cm^{-1}$.

N.M.R.: 7.60,s.,1H,$C_{(17)}H$; 6.87,s.,1H,$C_{(12)}H$; 6.30,s.,1H,$C_{(9)}H$; 4.33,t.,J=6 cps,2H,$CO_2CH_2$-; 3.84,s.,3H,$C_{(11)}OCH_3$; 2.90,s.,3H,N-$CH_3$; 2.16,s.,3H, $C_{(10)}CH_3$; 1.16,d.,J=7 cps,3H,$C_{(18)}H_3$.

M.S.=$M^+$ at 511.

EXAMPLE 6

2-pyrrolidinoethyl 1,10-dimethyl-2,7-dihydro-tetraphyllinate

For a period of 45 minutes, 10.23 g of $NaBH_3CN$ are added in small portions to a solution of 14.5 g of ethylpyrrolidine tetraphyllinate in 360 ml of trifluoracetic acid. After cooling with an ice bath, 145 ml of 37% formaldehyde, then 7.27 g of $NaBH_3CN$ are added dropwise with a vigorous agitation and under argon atmosphere.

The mixture is poured on ice, alkalized with ammonia, then depleted with methylene chloride. After washing with water, drying on $MgSO_4$ and vacuum dry evaporation, the extracts give a residue (10.5 g; yield: 68%) which is recrystallized in acetone.

Melting point: 144°–145° C. (acetone)

$a_D$: +78° (c=0.25; $CHCl_3$)

U.V. (methanol, c=15.64 mg/l) max: 212(4.54);241(4.31); 301(3.77). min: 228(4.26);275(3.24).

I.R. (KBr) bands at 1620 and 1710 $cm^{-1}$.

N.M.R: 7.63,s.,1H,$C_{(17)}H$; 6.88,s.,1H,$C_{(12)}H$; 6.28,s.,1H,$C_{(9)}H$; 4.33,t.,J=6 cps,2H,$CO_2$-$CH_2$; 3.83,s.,3H,$C_{(11)}OCH_3$; 2.88,s.,3H,N-$CH_3$; 2.13,s.,3H,$C_{(10)}H_3$; 1.13,d.,J=7 cps,3H,$C_{(18)}H_3$.

M.S.: $M^+$ at 495.

EXAMPLE 7

2-(N-methylpiperazine-ethyl)1,10-dimethyl-2,7-dihydro-tetraphyllinate (Ib)

For a period of 45 minutes, 9.54 of $NaBH_3CN$ are added in small portions to a solution of 13.64 g of N-methyl-piperazinoethyl tetraphyllinate in 340 ml of trifluoracetic acid. After cooling with an ice bath, 136 ml of 37% formaldehyde, then 6.82 g of $NaBH_3CN$ are added dropwise with vigorous agitation and under argon atmosphere.

The mixture is poured on ice, alkalized with ammonia, then depleted with methylene chloride. After washing with water, drying on $MgSO_4$ and vacuum dry evaporation, the combined extracts give a residue (11.21 g; yield: 77.5%) which is crystallized in ether.

Melting point: 147°–148° C. (ether)

$\alpha_D$: +68° (c=0.25; CHCl$_3$)

U.V. (methanol; c=14.66 mg/l) max: 212(4.52); 242(4.28); 301(3.80). min: 228(4.20); 275(3.35).

I.R. (KBr) bands at 1622 and 1698 cm$^{-1}$.

N.M.R.: 7.60,s.,1H,C$_{(17)}$H; 6.88,s.,1H,C$_{(12)}$H; 6.30,s.,1H,C$_{(9)}$H, 4.33,t.,J=6 cps,2H,CO$_2$CH$_2$-, 3.83,s.,3H,C$_{(11)}$OCH$_3$; 2.90,s.,3H,N$_{(1)}$CH$_3$; 2.57,s.broad,8H of the piperazine; 2.31,s.,3H,N'-CH$_3$; 2.15,s.,3H,C$_{(10)}$CH$_3$; 1.15,d.,J=7 cps,3H,C$_{(18)}$H$_3$.

M.S.: M$^+$ at 524.

EXAMPLE 8

2-piperidino-ethyl 1,10-dimethyl-2,7-dihydro-tetraphyllinate (Ic)

For a period of 45 minutes, 9.97 g of NaBH$_3$CN are added in small portions to a solution of 14.25 g of piperidinoethyl tetraphyllinate in 356 ml of trifluoroacetic acid. After cooling with an ice bath, 143 ml of 37% formaldehyde, then 7.12 g of NaBH$_3$CN are added dropwise with vigorous agitation and under argon atmosphere.

The mixture is poured on ice, alkalized with ammonia, then depleted with methylene chloride. After washing with water, drying on MgSO$_4$ and vacuum dry evaporation, the combined extracts give a residue (12.25 g or 81%) which is crystallized in ether.

Melting point: 137°–138° C. (ether)

$\alpha_D$: +77° (c=0.25; CHCl$_3$)

U.V. (methanol,C=14.49 mg/l) max: 212(4.60);242(4.42); 301(3.9). min: 228(4.34);275(3.47).

I.R. (KBr) bands at 1705 and 1620 cm$^{-1}$.

N.M.R.: 7.63,s.,1H,C$_{(17)}$H; 6.88,s.,1H,C$_{(12)}$H; 6.30,s.,1H,C$_{(9)}$H; 4.33,t.,J=6 cps,2H,CO$_2$CH$_2$; 3.87,s.,3H,C$_{(11)}$OCH$_3$; 2.93,s.,3H,N-CH$_3$; 2.16,s.,3H,C$_{(10)}$CH$_3$; 1.13,d.,J=7 cps,3H,C$_{(18)}$H$_3$.

M.S.: M$^+$ at 509.

EXAMPLE 9

1,10-dimethyltetraphylline (through DDQ)

At a temperature of 0° C., a solution of 5.80 g (1.5 equivalents) of 2,3-dichloro-5,6-dicyano-1,4-benzoquinone (DDQ) in 110 ml of dioxane is added dropwise to a solution of 7 g of dimethyl-1,10-dihydro-2,7-tetraphylline in a mixture of 35 ml of ether and 35 ml of dioxane. After agitation for 25 minutes, outside the cooling bath, the solution is diluted with ether and it is extracted four times with diluted ammonia. The ether is dried and concentrated under vacuum. The residue (6.41 g or a yield of 92%) crystallizes in methanol.

Melting point: 194°–195° C. (methanol)

$\alpha_D$: −112° (c=0.25, CHCl$_3$)

U.V. (methanol; c=15.40 mg/l) max: 231(4.65);300(3.93) min: 267(3.76) plateau: 280–282(3.82)

I.R. (KBr) bands at 1605 and 1705 cm$^{-1}$.

N.M.R.: 7.60,s.,1H,C$_{(17)}$H; 7.30,s.,1H,C$_{(12)}$H; 6.77,s.,1H,C$_{(9)}$H; 3.93,s.,3H,C$_{(11)}$OCH$_3$; 3.77,s.,6H, CO$_2$CH$_3$+N-CH$_3$; 2.35,s.,3H,C$_{(10)}$CH$_3$; 1.16,d.,J=7 cps, 3H,C$_{(18)}$H$_3$.

M.S.=M$^+$ at 410.

EXAMPLE 10

1,10-dimethyltetraphylline (through CuCl$_2$)

A solution of 550 mg of 1,10-dimethyl-2,7-dihydro-tetraphylline in 5 ml of pyridine is added to a suspension of 700 mg of CuCl$_2$ in 2 ml of pyridine. There is refluxed for 5 hours under argon atmosphere. There is diluted with water and extracted with ether. The organic phase is washed once with diluted ammonia and then dried and dry evaporated. 0.46 g of a residue (or 84%), which is crystallized in methanol, are obtained.

EXAMPLE 11

1,10-dimethyltetraphylline (air oxidation)

A solution of 1,10-dimethyl-2,7-dihydro-tetraphylline hydrochloride in methanol (500 mg) is left in open air for 3 days.

The solution is dry evaporated. After having been taken up with water, alkalized, extracted with methylene chloride and evaporated, the residue is separated on preparative silica plates with elution from NH$_3$ saturated CH$_2$Cl$_2$-CH$_3$OH mixture (99:1). The least polar product is the starting alkaloid. the most polar product is 1,10-dimethyltetraphylline.

EXAMPLE 12

Ethyl-piperidine dimethyl-1,10-tetraphyllinate

At a temperature of 0° C., a solution of 341 mg (1.5 m.moles) of DDQ in 3 ml of dry dioxane is added to 509 mg (1 m.mole) of ethyl-piperidine 1,10-dimethyl-2,7-dihydro-tetraphyllinate dissolved in a mixture of 7 ml of dioxane and 2 ml of ether.

After a half-hour, there is diluted with 200 ml of ether and the solution is then depleted with diluted ammonia. The dry evaporated ether gives a residue (450 mg; yield: 88%) which crystallizes in methanol.

Melting point: 150°–151° C.

U.V. (methanol; C=14.95 mg/l): max: 232(4.33); 301(3.58); min: 269–276 (3.43); plateau: 280–287 (3.47).

I.R. (KBr) bands at 1618 and 1690 cm$^{-1}$

M.S.: M$^+$ at 507.

EXAMPLE 13

Ethyl-morpholine-1,10-dimethyl-tetraphyllinate

At a temperature of 0° C., a solution of 341 mg (1.5 m.moles) of DDQ in 3 ml of dry dioxane is added to 511 mg (1 m.mole) of ethyl-morpholine 1,10-dimethyl-2,7-dihydro-tetraphyllinate dissolved in a mixture of 7 ml of dioxane and 2 ml of ether.

After a half-hour, the reaction is completed. There is diluted with 200 ml of ether and the solution is depleted with diluted ammonia.

The dry evaporated ether gives a residue (400 mg; yield: 78.6%) which crystallizes in methanol.

Melting point: 168°–169° C. (methanol)

U.V. (methanol;C=16.11 mg/l) max: 234(4.63); 299(3.91); min: 270–273(3.77); plateau: 279–286 (3.82).

I.R. (KBr) bands at 1615 and 1695 cm$^{-1}$.

M.S.: M$^+$ at 509.

What I claim is:

1. Oxayohimbanes having the formula:

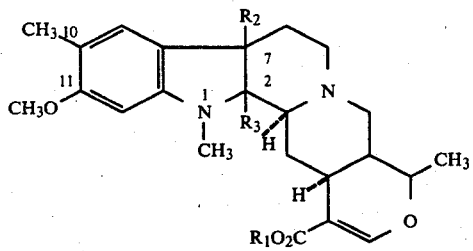 (I)

wherein $R_1$ is selected from the group consisting of an alkyl group having 1 to 8 carbon atoms, dialkyl aminoalkyl group having 1 to 8 carbon atoms and wherein $R_2$ and $R_3$ are hydrogen atoms, wherein dialkylamino can form pyrrolidino or piperidino and pharmaceutically acceptable mineral or organic acid addition salts thereof.

2. A compound according to claim 1, which is the 1,10-dimethyl-2,7-dihydro-tetraphylline.

3. A compound according to claim 1, which is diethylamino-ethyl 1,10-dimethyl-2,7-dihydro-tetraphyllinate.

4. A compound selected from the group consisting of:
2-dimethylaminoethyl 1,10-dimethyl-2,7-dihydro-tetraphyllinate
2-piperidinoethyl 1,10-dimethyl-2,7-dihydro-tetraphyllinate
2-diethylaminoethyl 1,10-dimethyl-2,7-dihydro-tetraphyllinate or a pharmaceutically acceptable acid addition salt thereof, as claimed in claim 1.

5. A pharmaceutical composition for the treatment of cardiac arrhythmia comprising an effective amount an oxayohimbane having the formula

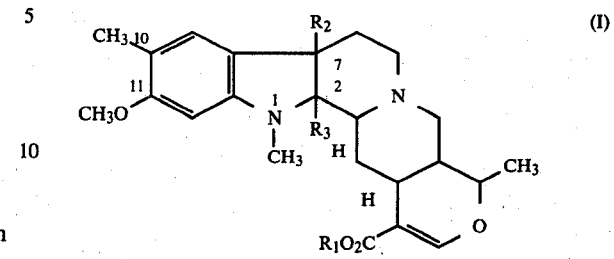 (I)

wherein $R_1$ is selected from the group consisting of an alkyl group having 1 to 8 carbon atoms, and dialkylaminoalkyl group having 1 to 8 carbon atoms or and wherein $R_2$ and $R_3$ are hydrogen atoms, wherein dialkylamino can form pyrrolidino or piperidino and pharmaceutically acceptable mineral or organic acid addition salts thereof and a pharmaceutically acceptable carrier.

6. A composition according to claim 5 which has 1,10-dimethyl-2,7-dihydro-tetraphylline as the effective compound.

7. A pharmaceutical composition according to claim 5 in the form of tablets, capsules or solute in unit doses from 1 to 100 mg of active product being taken in one or several daily or occasional doses, if desired in combination with auxiliary agents, diluents, vehicles or excipients conventionally used for pharmaceuticals.

8. The process for treating disorders of the heart rhythm of mammals wherein a pharmaceutical composition as claimed in claim 5 is used.

* * * * *